United States Patent [19]

Martin

[11] Patent Number: 5,078,739
[45] Date of Patent: Jan. 7, 1992

[54] BILEAFLET HEART VALVE WITH EXTERNAL LEAFLETS

[75] Inventor: Richard L. Martin, San Diego, Calif.

[73] Assignee: Janus Biomedical, Inc., Austin, Tex.

[21] Appl. No.: 554,902

[22] Filed: Jul. 20, 1990

[51] Int. Cl.⁵ .................. A61F 2/24; A16K 15/00; A16K 17/00; A16K 21/04
[52] U.S. Cl. ........................................ 623/2; 137/512; 137/527
[58] Field of Search .................. 623/2; 137/512, 527, 137/527.8, 527.2

[56] References Cited

U.S. PATENT DOCUMENTS

| | | | |
|---|---|---|---|
| 3,589,392 | 6/1971 | Meyer | 137/525.1 |
| 4,017,911 | 4/1977 | Kafesjian et al. | 623/2 |
| 4,114,202 | 11/1978 | Roy et al. | 623/2 |
| 4,178,638 | 12/1979 | Meyer | 623/2 |
| 4,263,680 | 4/1981 | Reul et al. | 623/2 |
| 4,373,216 | 2/1983 | Klawitter | 623/2 |
| 4,878,909 | 11/1989 | Parravicini | 623/2 |

Primary Examiner—Ronald Frinks

[57] ABSTRACT

An improved heart valve prosthesis (20) suited for replacement of any of the four valves in the heart. The invention includes a generally annular orifice ring (22) having a fluid flow bore with a smooth inner wall (26) through which blood flows, controlled by two pivoted leaflet occluders (40), supported at the downstream edge of the orifice ring.

The occluders are supported at the outboard edges of the orifice ring, overlapping the fluid flow bore and generally about each other to seal backflow and regulate flow in one direction only. Occluder travel is limited by bending moment resistance of the occluder hinge and lateral blood flow. Occluder hinges are unloaded at a point between fully opened and fully closed.

The bearing surfaces between the occluder means and the annular orifice are wide enough to allow the valve to be constructed from materials of different hardnesses.

4 Claims, 5 Drawing Sheets

Section 2-2

BILEAFLET HEART VALVE WITH EXTERNAL LEAFLETS

BACKGROUND

1. Field of the Invention

This invention relates to fluid check valves, specifically to an improved prosthetic mechanical heart valve intended for replacement of human heart valves.

2. General

Since the 1960's, surgical replacement of diseased natural heart valves has become safer and more practical. These prostheses, which function as fluid check valves, are actuated by the pumping action of the heart. It is essential that in order to function as long-term life-support devices, such valves must satisfy the following requirements: complete biocompatibility, high fluid efficiency, extreme reliability, outstanding durability and resistance to wear.

The valve must be constructed to withstand approximately 40 million opening and closing cycles per year under the unceasing pumping of the human heart. Blood flow through the valve must not be restricted and the valve function must under all circumstances not be destructive to the blood that is pumped therethrough. The valve prosthesis must not place unnecessary stress on the heart. Furthermore, the valve must be designed in such a way as to minimize the often fatal side effect of thromboembolism, or the formation and liberation of a blood clot from the prosthetic valve. It is currently a recognized therapy that all patients receiving mechanical heart valve replacements must take anticoagulant drugs to reduce the potential of a thromboembolic event.

3. Description of Prior Art

Heretofore, a wide variety of mechanical heart valves have been designed and developed around this area of bioengineering endeavor. Reference is made hereby to an important body of this literature. Nevertheless, existing prosthetic valves fall short of an ideal substitute for the healthy, natural heart valves, and work continues to improve the functioning of these valves to make them even more reliable, efficient and resistant to the formation of blood clots. Most notably, none of the existing devices work like the natural valves, instead placing the valving mechanisms inside the valve body itself.

All of these devices function as one-way check valves, and have one or more occluder members to seal the valve, preventing reverse flow. Devices now in use generally place the occluding members and the supports or restraints for those occluders in the path of the blood flow when the valve is open. This design aspect increases the resistance to fluid flow by reducing the effective unobstructed orifice area compared to the tissue implant diameter, which seriously reduces the hydraulic efficiency of the device. It further prohibits the possibility of tissue ingrowth, which, while it could greatly reduce the thromboembolic potential of the device, would interfere with free movement of the occluder(s).

The first successful mechanical valves were "ball-in-cage" valves, and were made with a mobile poppet that was pushed to and fro with the blood pumped through the heart. U.S. Pat. No. 3,365,728 to Edwards et al (1968) discloses a valve where the sealing action is accomplished by a soft poppet which is restrained by a metallic cage. The literature has shown that in actual use, blood clots form on the stationary cage and that the resistance to forward flow around the poppet is high. While the poppet is displaced downstream when blood is flowing through the valve, this design is still obstructive to free flow as the blood must still change directions and flow around the ball.

The next major advance in this technology was the introduction of the "tilting-disc" valve, a device where a discoid occluder was suspended in a ring and rocked open and closed with blood flow. U.S. Pat. No. 3,824,629 to Shiley (1974) discloses valve with a tilting saucer-shaped occluder suspended in a cage. This design, while an improvement over the ball valves, still placed the occluder in the flow path during forward flow, resulting in a significant pressure drop across the valve. Thrombosis problems (total valve obstruction by blood clots) have been reported with this type of valve.

In an effort to reduce the pressure drop across the valve, the occluder was split into two pieces, each being separately pivoted. U.S. Pat. No. 4,689,046 to Bokros (1987) discloses a representative example of these twin-occluder or "bileaflet" valves with the occluder pivots riding in depressions within an annular body. This design represented a further improvement in flow resistance reductions, but the occluders are still in the flow stream when open. This type of design still exhibits the problems of blood clots forming in the stagnant areas of the pivot depressions. Further, these designs concentrate the bearing and rotational wear in the pivot into very small areas, and extremely hard materials, such as pyrolytic carbon are required to effect adequate durability of these prostheses. Besides being very hard, pyrolytic carbon is also brittle and fractures of this material which caused failure of this type of valve have been reported.

There are also other problems common to existing designs in current use. The valves with a mobile central leaflet or leaflets have been shown to become stuck on surgical sutures or subvalvular tissues within the heart. This extrinsic interference is a result of a foreign body becoming jammed between the disc or leaflets and the orifice ring, and results in failure of the valve to function. Therefore, tissue ingrowth into the valve must be prevented as it would interfere with the operation of the valve. This is a disadvantage, because if a prosthesis could be covered with the heart's own lining, it would be as thrombus-free as the heart itself.

Also, valves with centrally-mounted occluders, particularly the "tilting-disc" valves, must be precisely oriented within the heart to produce the best flow characteristics. Finally, all of the mechanical heart valve prostheses in use today still require the recipient to take anticoagulant drugs to minimize the risk of thromboembolism. This is due to a design feature in each of these valves that creates a region of stagnation where blood clots can nucleate. In some designs, this is in a recess in the pivot region, in others it is behind a non-mobile cage or supporting structure of the valve.

Few exceptions to locating the occluder means out of the field of flow are found. U.S. Pat. No. 3,589,392 to Meyer (1971) discloses a split leaflet valve where the leaflets are hinged at the outer edge, but the leaflet assembly is contained in a thick external tube that would greatly reduce the ratio of flow area to tissue annulus implant diameter. The leaflets are very high in profile and therefore likely to contact structures within the heart on opening. Also, the leaflets are allowed to open to 90° and reverse flow through the valve would run parallel to the fully open leaflets, not necessarily creating enough force on them to make them swing closed. Finally, if the valve was oriented the slightest bit out of exact alignment with the flow stream, one of the leaflets would positively be held open by reverse flow defeating its function as a check valve.

U.S. Pat. No. 4,114,202 to Roy et al (1978) shows an embodiment where the leaflets are hinged at the outboard edge, but the leaflets remain in the throat area of the thick annular body of the valve, still obstructing flow. U.S. Pat. No. 4,178,638 to Meyer (1979) discloses a fluid check valve that is hinged at the outer edges, but the hook forming the hinge requires the use of a recessed well, creating a large, vacant area of stagnation which would invite the formation of blood clots. The hinge design here concentrates wear on the tip of the restraining edge of the hook, and is therefore unsuitable for the countless opening and closing cycles exerted on a heart valve. Also, the stationary downstream ring required to restrain the leaflets in the cardiac application would further invite the formation of blood clots as seen with the ball valves, and the use of soldered assemblies has not provide suitable for demanding implant applications.

U.S. Pat. No. 4,263,680 to Reul et al (1981) discloses a single leaflet valve with an external hinge, but the distance the full diameter occluder must traverse between fully open and fully closed would cause backflow through the device to be unacceptably high. Also, there is nothing to restrain the occluder member from over-rotating beyond 90°, and therefore not closing, defeating its function as a check valve. Further, protrusion of the full diameter edge-hinged disc into the chambers of the heart would likely contact structures inside the heart, damaging the heart tissues and obstructing valve function.

OBJECTS AND ADVANTAGES

Accordingly, the objects of my invention are
(a) to provide an improved heart valve prosthesis which is suited primarily for replacement of the aortic valve or mitral valve but will work with any of the four valves in the heart;
(b) to provide an improved heart valve where the occluder mechanism does not obstruct forward flow of blood through the valve;
(c) to provide an improved heart valve that is free from small areas of concentrated wear so that a variety of alternative materials can be employed;
(d) to provide an improved heart valve requiring only limited occluder travel between the fully opened and fully closed positions;
(e) to provide an improved heart valve with rapidly opening and closing leaflets;
(f) to provide an improved heart valve with as few seams and joints as possible to minimize the potential for thromboembolism formation due to blood stagnation;
(g) to provide an improved heart valve with simplified stops to limit leaflet opening motion to ensure positive closure;
(h) to provide an improved heart valve with no areas of stagnation during forward flow;
(i) to provide an improved heart valve which will more closely approximate the function of the natural heart valve;
(j) to provide an improved heart valve with greater freedom from malfunction due to entrapment of tissue and sutures in the valve mechanism;
(k) to provide an improved heart valve with greater freedom from malfunction due to ingrowth of tissue into the valve mechanism;
(l) to provide an improved heart valve with flow characteristics unaffected by the orientation of the valve within the heart;
(m) to provide an improved heart valve with a very large ratio of orifice flow area to tissue implant diameter;
(n) to provide an improved heart valve which can be made from a wide variety of materials;
(o) to provide an improved heart valve with an even distribution of pressure on the leaflets;

Further objects and advantages of my invention will become apparent from a consideration of the drawings and the ensuing description of it.

Figure 1:
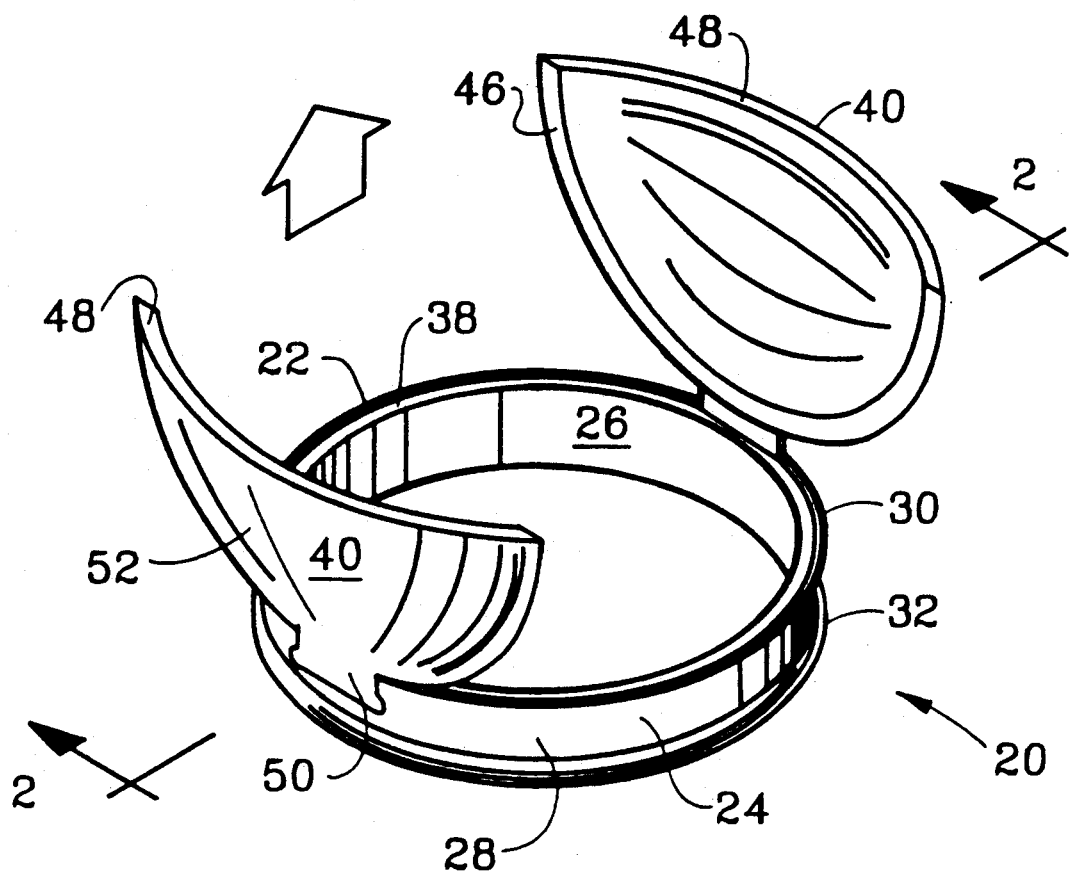
FIG. 1 is a perspective view of a bileaflet heart valve embodying various features of the invention, shown in the open position.

LIST OF REFERENCE NUMERALS IN DRAWINGS 20 heart valve
22 orifice ring
24 exterior surface
26 interior surface
28 flat surface
30 upper ring
32 lower ring
34 upstream section
36 downstream section
38 flat surface
40 leaflet assembly
42 upstream surface
44 downstream surface
46 flat edge
48 abutment surface
50 hinge
52 mobile portion
54 ridid section
55 thin section
56 raised section
58 boss
60 recess
62 elongated recess
64 parallel faces
66 reinforcing member
68 synthetic layer
70 bottom section 120 heart valve
122 orifice ring (fragment)
124 exterior surface
126 interior surface
128 flat surface
130 upper ring
132 lower ring
138 flat surface
140 leaflet (fragment)
146 flat surface
148 abutment surface
150 pivot knuckle
152 pivot bore
154 foot
160 pivot journals
162 journal bore
170 pin

DESCRIPTION OF THE INVENTION FIGS. 1-5

Figure 2:
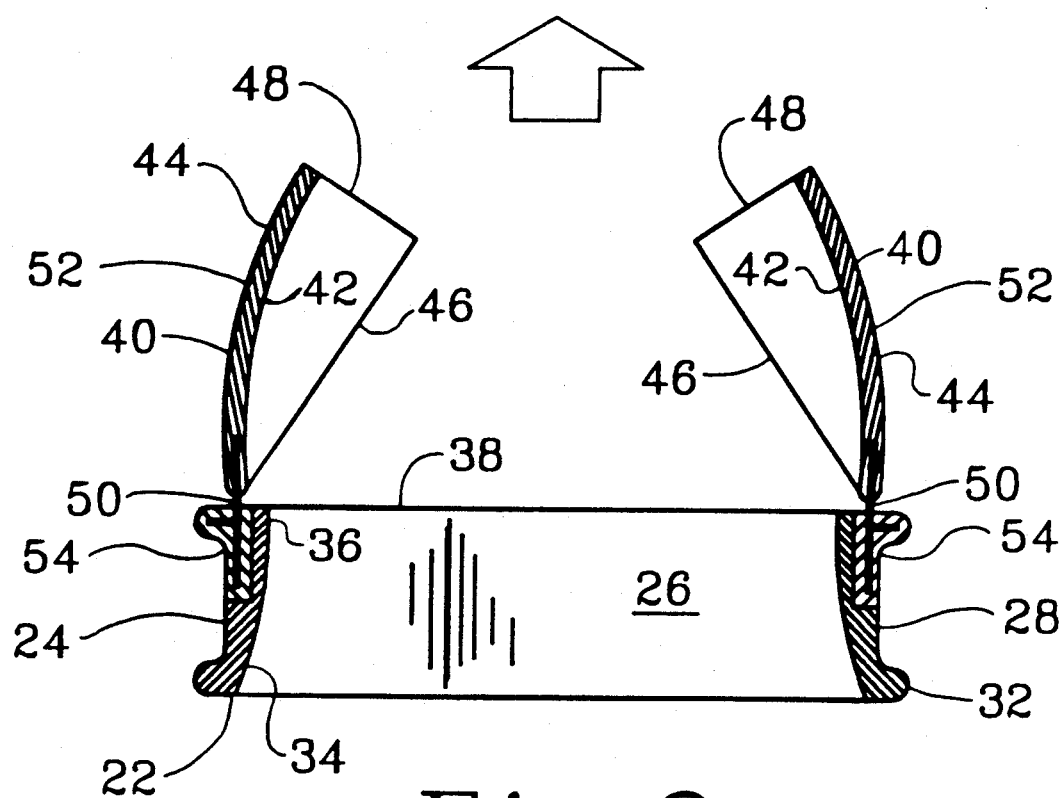
FIG. 2 is an enlarged sectional view taken generally along the line 2—2 shown in FIG. 1.

FIG. 1 shows an overall view of a heart valve 20 of the invention, which consists of an annular body 22 also referred to as an orifice ring which supports a pair of freely pivoting occluders or leaflets 40 that open and close to regulate the blood flow through a central passageway which is defined by an interior surface 26 of orifice ring 22. FIG. 2 shows a section view of heart valve 20 taken generally along the line 2—2 in FIG. 1. In the bileaflet configuration, heart valve 20 is bilaterally similar around a vertical centerline drawn through FIG. 2, so discussion of design and operation will be confined to one half of the valve.

Orifice ring 22 is illustrated with an exterior surface 24 comprising a flat section 28 which is a section of a right circular cylinder, bounded by an upper concentric ring 30 and a lower concentric ring 32. Upper ring 30 and lower ring 32 constrain a suitable fabric ring encircling flat section 28, for use in sewing valve 20 into the heart tissues. However, in as much as the sewing ring forms no part of the present invention, it is simply omitted so as to facilitate the illustration of the specific components of the heart valve with which the invention is concerned.

As seen best in FIG. 2, the cross-section of orifice ring 22 has a downstream section 36 which is thicker than an upstream section 34. A flat surface 38 is formed normal to downstream section 36 of interior surface 26. Flat surface 38 is the widest portion of the section of orifice ring 22. The central passageway defined by interior surface 26 is completely smooth and uninterrupted by occluders or support means. The contour of interior surface 26 need not be round and can therefore be of any desired shape.

Still referring to FIG. 2, leaflet assembly 40 consists of a mobile portion 52, connected to a projection means having a rigid section 54 and a hinge 50 defining a flexible section. The projection means extend generally outwardly from the flat edge 46 of the occluders 40 and have a rigid section 54 which is receved within the recess means 60. Mobile portion 52 comprises an upstream surface 42, a downstream surface 44, an abutment surface 48 and a flat edge 46, which when closed, seats against corresponding flat surface 38 of orifice ring 22. These mating surfaces may alternatively slope inward, outward, and be either concave or convex to aid in centering of mobile portion 52 when closed. Mobile portion 52 is preferentially a section of a sphere, but can alternatively be a section of a right circular cylinder, a plane or any other suitable shape.

Figure 3:
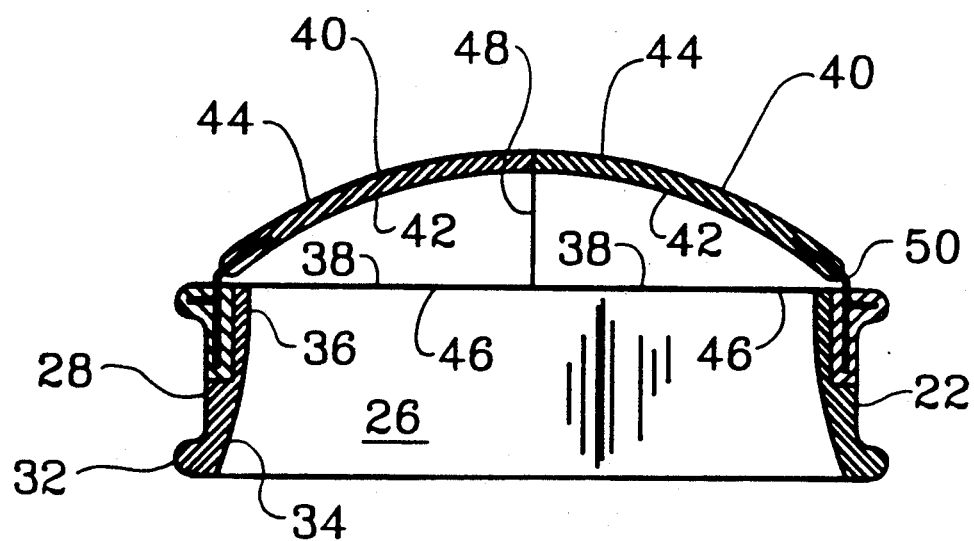
FIG. 3 is a sectional view similar to FIG. 2, but with the leaflets shown in the closed position.

As best depicted in FIG. 2 and 3, abutment surface 48 is oriented at an angle to leaflet downstream surface 44 so that abutment portions 48 meet in substantially face-to-face contact when both leaflets 40 are in the closed position. This effectively seals valve 20 along its diameter when closed.

Figure 4:
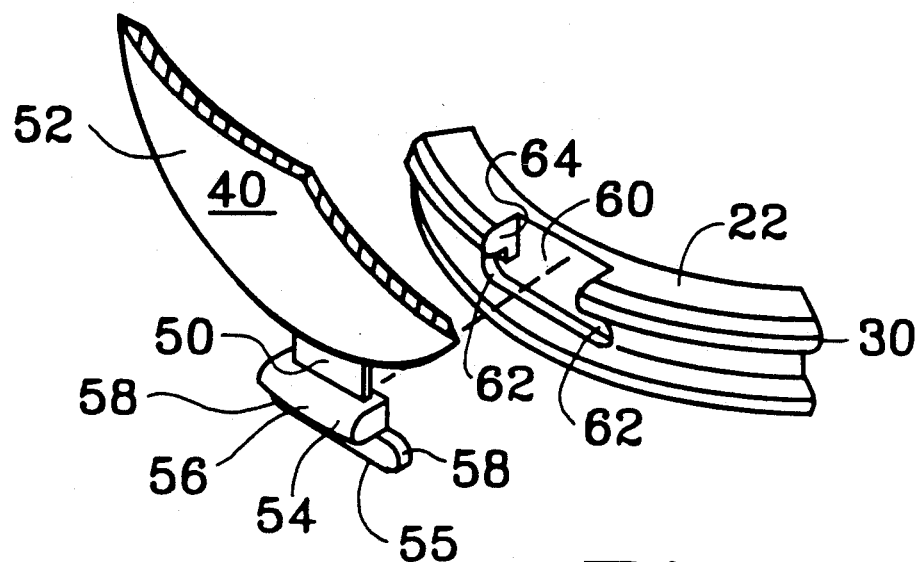
FIG. 4 is an exploded drawing of the leaflet to orifice assembly of the valve of FIG. 1.

FIG. 4 is an exploded view of the assembly of leaflet assembly 40 and orifice ring 22, with only fragmentary portions of leaflet 40 and orifice ring 22 illustrated. Rigid section 54 comprises an upper raised section 56 and a thin section 55. Thin section 55 comprises a boss 58 at each end. Orifice ring 22 contains a flat-bottomed recess 60 the outline of which is defined by an elongated section 62 and two parallel faces 64. Rigid section 54 of leaflet 40 is inserted into recess 60 with a close press fit. When fully assembled, raised section 56 matches the profile of upper ring 30, a portion of which is removed in creating recess 60. Bosses 58 engage elongated section 62 of recess 60 to prevent operational forces on leaflet 40 from pulling free of orifice ring 22. Rigid section 54 is overlaid by and held in final position with the fabric suture ring (not illustrated) which is fitted between upper and lower concentric rings 30 and 32. Thus, the fabric suture ring prevents rigid section 54 from backing out of recess 60, effectively locking leaflet 40 and orifice ring 22 together.

Figure 5:
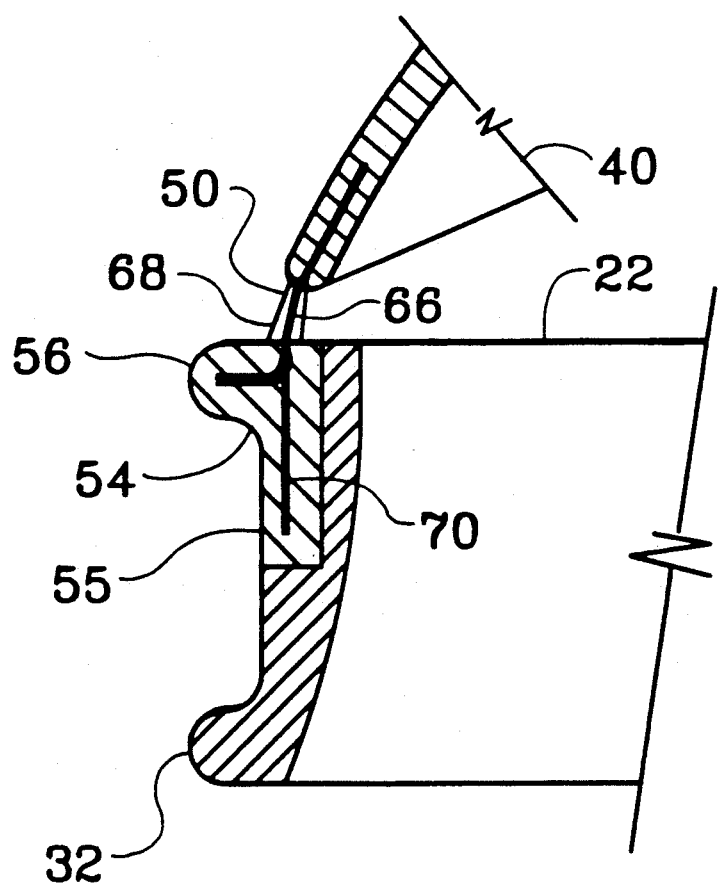
FIG. 5 is an enlarged fragmentary sectional view of one side of the hinge mechanism, taken generally along the line 2—2 in FIG. 1.

FIG. 5 is a fragmentary section detailing hinge 50 seen in the left side of FIG. 2. Hinge 50 is composed of a reinforcing member 66, preferentially made of synthetic fibers, and a synthetic layer 68 preferentially made of polyurethane or similar biocompatible polymers. However, hinge 50 may also be compose of thin sections of fatigue-resistant alloy or synthetics. Hinge 50 is constructed so that in its relaxed state, mobile portion 52 is held at an angle between the fully opened and fully closed positions, as depicted by the position of leaflet fragment 40 as shown in FIG. 5. Synthetic layer 68 is used to bond the layers of reinforcing member 66 together, and also to provide a biocompatible lubricating coating on reinforcing member 66.

Reinforcing member 66 is firmly bonded into synthetic layer 68, mobile portion 52 and rigid section 54, permanently connecting them. Rigid section 54 is made of a hard biocompatible polymer molded over a bottom section 70 of reinforcing member 66 and anchors hinge 50 firmly into orifice ring 22 through bosses 58 which engage in elongated recess 62. Reinforcing member 66 is similarly bonded into mobile portion 52.

Orifice ring 22 and leaflets 40 may be made of any biocompatible and non-thrombogenic material that will take the wear to which the device will be subjected to during approximately 40 million opening and closing movements of leaflets 40 during each and every year that valve 20 is implanted. Orifice ring 22 is preferentially made from a porous rigid material, such as textured titanium, to stimulate ingrowth of the natural heart lining. It can, however, be made from any suitable material that is biocompatible and non-thrombogenic, including polymers, a pyrolytic carbon-coated substrate, solid pyrolytic carbon, metals, ceramics, or synthetics. Leaflets 40 may be made of similar materials.

OPERATION OF THE INVENTION FIGS. 1-5

The permissible flow of blood through heart valve 20 is in one direction only, which is upward in the orientation in which the valve is shown in FIGS. 1, 2 and 3, and is as shown by the large arrow which appears at the top of FIG. 1 and 2. It should, of course, be understood that valve 20 can operate in any physical orientation and its function or operation is not significantly affected by gravity. Thus, the terms such as inflow and outflow, as used hereinafter, are merely employed to facilitate explanation and understanding and are not meant to place any limitations upon the operation of the heart valves being described.

When fully open, each leaflet 40 is held open by the forward flow of blood. In the open position depicted in FIG. 2, leaflets 40 lie at an angle of about 5° to 40° to the centerline of the cylindrical valve passageway defined by inner surface 26. Leaflets 40 are allowed to swing fully out of the way of forward flow. Blood may therefore flow out of the central passageway completely unobstructed.

One of the functions of reinforcing member 66 of hinge 50 is to provide a measure of strength and rigidity to the pivot function. This rigidity creates a small opposing bending moment in hinge 50 when leaflet 40 is mounted in orifice ring 22 is then displaced from its rest position. In this way no contacting stop mechanism is required to limit leaflet motion.

When the outflow of blood through the valve ceases, and begins to move in the reverse direction in response to the cyclic pumping action of the heart, the small bending moment created in hinge 50 by the forward flow of the blood holding leaflets 40 in the open position begins to cause leaflets 40 to pivot toward the closed position. As the blood flow actually begins to reverse, blood pressure on leaflet downstream surface 44 moves leaflet 40 to the fully closed position as shown in FIG. 3.

When the closed position is reached as depicted in FIG. 3, flat edges 46 of leaflets 40 lie in contact with flat surface 38 on orifice ring 22. As leaflets 40 are held displaced downstream from their rest position by the differentially higher blood pressure on downstream side 44 compared to upstream side 42, a small opposing bending moment in hinge 50 is created. When the blood pressure differential across the valve drops to zero as flow changes back to discharge or forward flow, this small bending moment in hinge 50 assists leaflets 40 in swinging towards the fully open position. This results in a lower pressure required to open the valve.

As leaflets 40 do not move within orifice ring 22, there is no chance of a foreign body coming between them and obstructing free motion of leaflets 40. Therefore, the heart tissue can be allowed to grow over and cover orifice ring 22, the leaflet motion will not be affected.

DESCRIPTION OF THE INVENTION FIGS. 6-7

Figure 6:
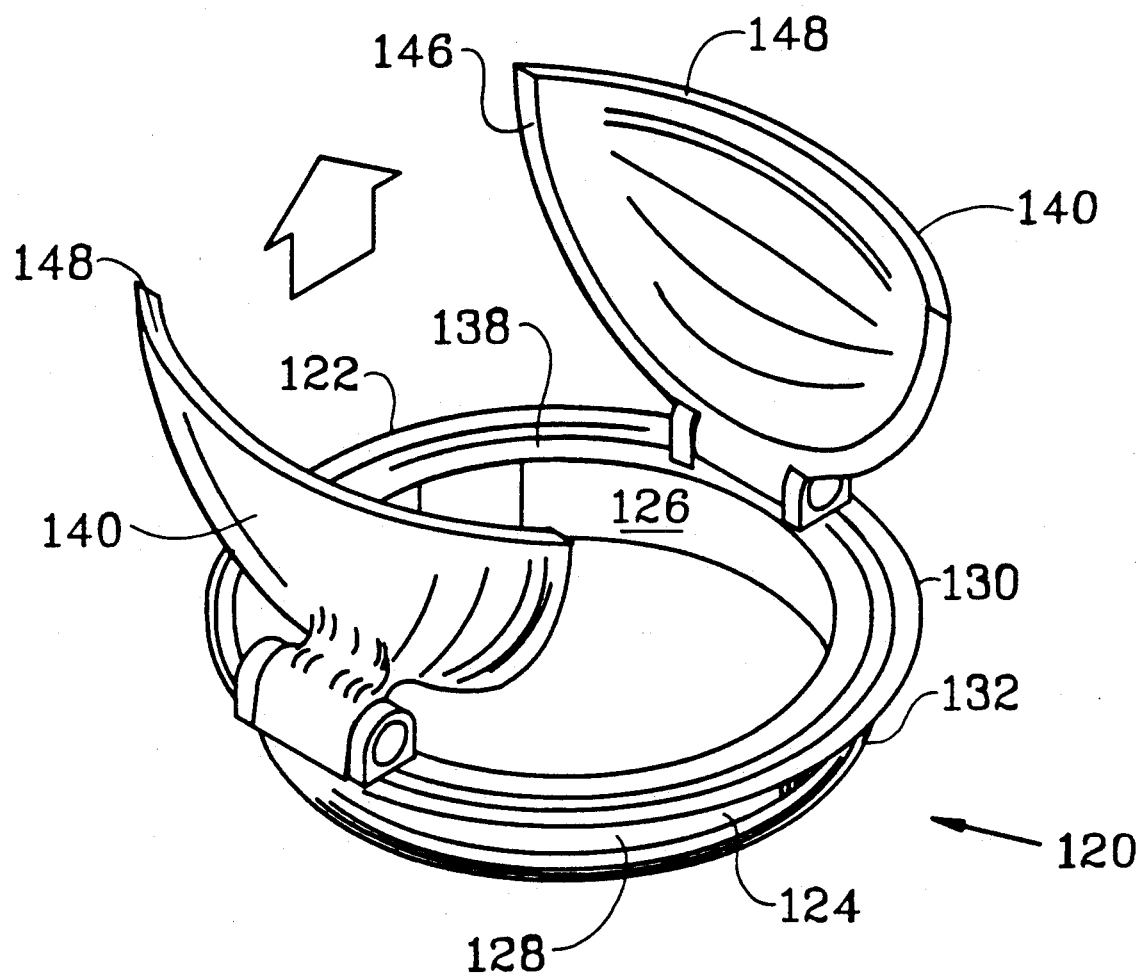
FIG. 6 is a perspective view of an alternative embodiment of another bileaflet valve.
Figure 7:
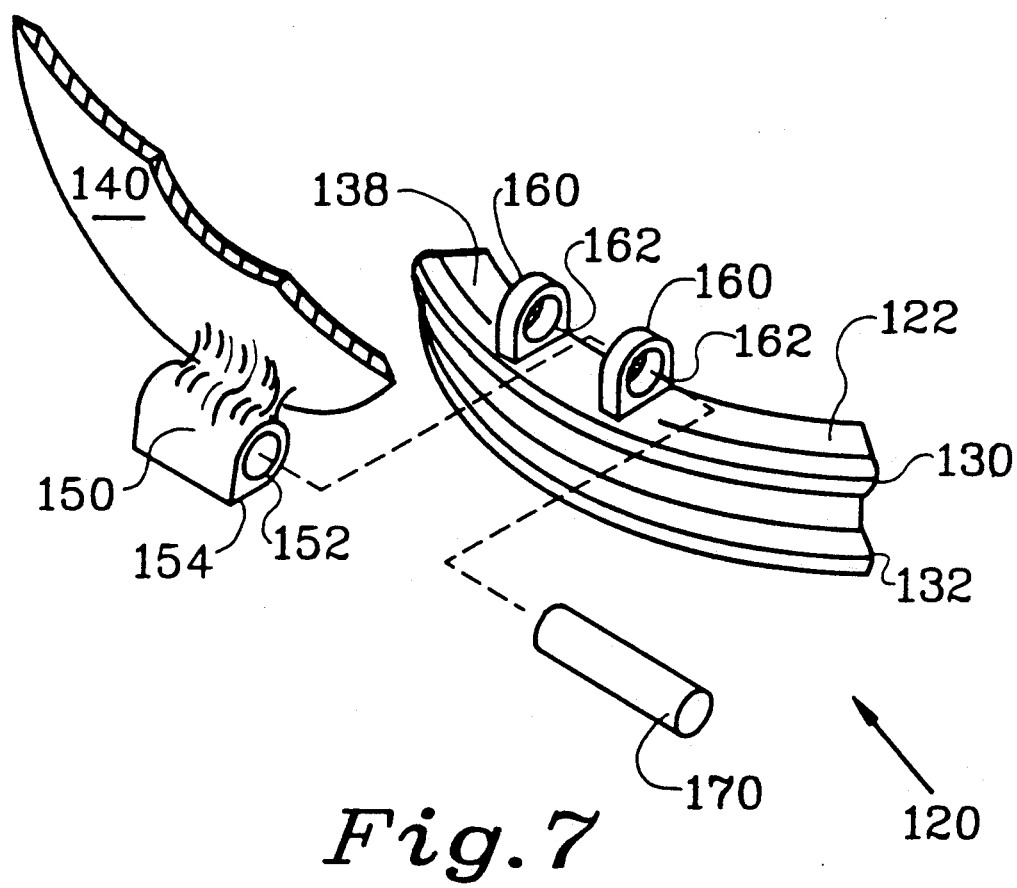
FIG. 7 is an exploded drawing of the leaflet to orifice assembly of an alternate embodiment of the valve shown in FIG. 6.

Depicted in FIGS. 6-7 of the drawings is an alternative embodiment of a heart valve 120 which includes an orifice ring 122 designed to operate with a pair of rigid leaflet occluders 140. Generally, the same principles of design are executed in the heart valve 120 as were hereinbefore explained in detail with respect to heart valve 20, and therefore similar numbers in the 100 series are utilized to refer to comparable components. Moreover, it should be understood that, unless specifically stated hereinafter, the function and construction of the comparable components will be essentially the same as previously described.

Referring to FIG. 6 and 7, orifice ring 122 has an interior surface 126 which defines the passage or orifice through which the bloodstream will flow. Orifice ring 122 also has an exterior surface 124 and is illustrated with a similar arrangement to that hereinbefore described with an upper concentric ring 130 and a lower ring 132, separated by a flat surface 128. There is likewise a similar flat face 138 on orifice ring 122 and flat surfaces 146 and abutment surface 148 on leaflet 140. The hinge mechanism does differ substantially from that of the previously mentioned version as described in detail hereinafter.

Each leaflet 140 covers approximately one-half of orifice ring 122. In this embodiment, leaflet 140 is made of a single rigid material, such as pyrolytic carbon or another rigid synthetic. Situated on a downstream flat edge 138 of orifice ring 122 are two pairs of diametrically opposed pivot journals 160. Each pivot journal 160 has a bore 162 therethrough, such that bores 162 in journals 160 are aligned along centerlines.

Leaflet 140 is fabricated with a pivot knuckle 150 and a bore 152 therethrough. Pivot knuckle 150 is generally circular in section, but also comprises a foot 154 at the outboard edge. Assembly of leaflet 140 to orifice ring 122 is accomplished by placing leaflet 140 between pivot journals 160 and inserting a pin 170. Pin 170 may be sized so that it is a light press fit in journal bore 162 and a loose running fit in leaflet bore 152, or vice versa. Thus, the wear from leaflet 140 pivoting around pin 170 is spread over a large area increasing the variety of materials that can be used for leaflet 140, pin 170 and orifice ring 122.

OPERATION OF THE INVENTION FIGS. 6-7

Leaflet motion in response to blood flow is similar to that described hereinbefore. Leaflets freely pivot open or closed in response to differential blood pressure produced by the contractions of the heart.

In the invention shown in FIG. 7, leaflet 140 is assembled to orifice ring 122 by pivot pin 170 placed through leaflet bore 152 and pivot journal bores 162. Leaflet position on opening is limited by contact of foot 154 of leaflet 140 with flat surface 138 on orifice ring 122. The closing motion of leaflets 140 is limited by contact of leaflet 140 with flat surface 138 of orifice ring 122.

In neither of these inventions do the leaflets move within the orifice ring and create a mechanism for a foreign body to obstruct free motion of the leaflets. Consequently, heart tissue can be allowed to grow over and cover the orifice ring and the leaflet motion will be unaffected. Further, blood flow through the open valve orifice ring is likewise unobstructed by the leaflets.

Although the invention has been described with regard to two preferred embodiments, it should be understood that various changes and modifications as would be obvious to one having the ordinary skill in this art may be made without departing from the scope or spirit of the invention which is defined by the claims appended hereto. For example, with respect to many of the novel features of the invention, the occluders which are shown in various of the embodiments need not be spherical but could be curved or flat in cross-section. Also, these same principles while detailed above only for a double leaflet valve, could be applied to a valve with three leaflets.

Particular features of the invention are emphasized in the claims that follow.

I claim:

1. A fluid check valve comprising
   a generally annular orifice ring which has a smooth interior surface that defines a central passageway for blood flow therethrough, a pair of oppositely disposed, flow-actuated occluder means supported on said orifice ring for alternately blocking and then allowing the flow of blood through said passageway in a predetermined direction, a pair of recess means projecting generally radially inward from exterior surface of said orifice ring, which recess means are placed at locations generally diametrically opposing one another and have at least one elongated section, projections means extending generally outward from edge of each said occluder means which are receivable within said recess means, said projection means containing a hinge means comprising a flexible section, said flexible supporting said occluder means for pivotal movement and comprising a stop means to limit opening travel of said occluder means, seating means substantially about a downstream edge of said orifice ring, on which said occluder means are receivable when in the fully closed position, whereby said occluder means do not obstruct the free flow of blood through said passageway when said occluder means are in the open position.

2. The fluid check valve of claim 1 wherein said hinge means is composed of synthetic fibers and polymers.

3. The fluid check valve of claim 1 wherein said inner surface of said orifice ring is treated to encourage ingrowth of the heart's own inner lining.

4. The fluid check valve of claim 1 wherein said annular orifice ring is not round.

* * * * *